(12) United States Patent
Mao et al.

(10) Patent No.: US 6,908,765 B1
(45) Date of Patent: Jun. 21, 2005

(54) POLYPEPTIDE—HUMAN SR SPLICING FACTOR 52 AND A POLYNUCLEOTIDE ENCODING THE SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 243 days.

(21) Appl. No.: 10/130,798

(22) PCT Filed: Nov. 20, 2000

(86) PCT No.: PCT/CN00/00461

§ 371 (c)(1),
(2), (4) Date: May 23, 2002

(87) PCT Pub. No.: WO01/38386

PCT Pub. Date: May 31, 2001

(30) Foreign Application Priority Data

Nov. 23, 1999 (CN) ........................................ 99124073 A

(51) Int. Cl.[7] ................................................ C12N 5/16
(52) U.S. Cl. .................... 435/358; 435/365; 435/320.1; 435/252.33; 536/23.5
(58) Field of Search ................................. 435/358, 365, 435/320.1, 252.33; 536/23.5; 514/44

(56) References Cited

FOREIGN PATENT DOCUMENTS

WO 97/28186 8/1997

OTHER PUBLICATIONS

Verma et al., Nature, vol. 389, Sep. 18, 1997, pp. 239–242.*
Anderson, Nature, vol. 392 suppl., Apr. 30, 1998, pp. 25–30.*
Juengst, BMJ, vol. 326, Jun. 28, 2003, pp. 1410–1411.*
International Search Report for PCT/CN00/00461.

* cited by examiner

*Primary Examiner*—James Ketter
(74) *Attorney, Agent, or Firm*—Crowell & Moring LLP

(57) ABSTRACT

The present invention discloses a novel polypeptide-human SR splicing factor 52 and polynucleotide encoding the same, as well as a method of producing the polypeptide by DNA recombinant technology. The present invention also discloses methods of using the polypeptide in treatment of various disease, such as malignant tumor, blood disease, HIV infection, immunological disease and various inflammation. The present invention also discloses an antagonist againts the polypeptide and the therapeutic use of the same. The present invention also discloses the use of such polynucleotide encoding Human SR splicing factor 52.

7 Claims, 2 Drawing Sheets

Figure 2:
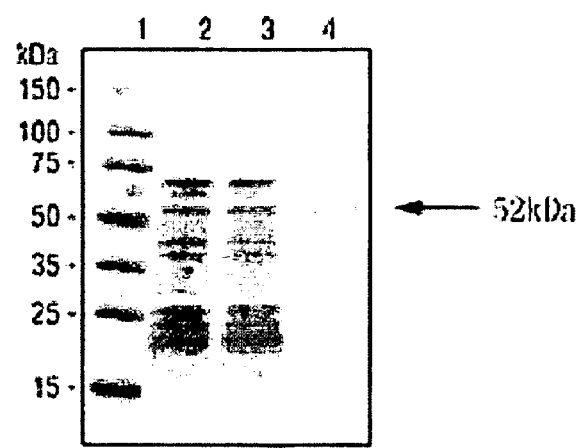

Identity = 207/275 (75%), Similarity = 243/275 (88%)

```
Human SR Splicing    195 RMFGSGREHNFTRPNEKGEYEVAEGIGSTVFRAILDYYKTGIIRCPDGISIPELREACDY 254
Factor 52:               RMFG GRE+NFTRPNEKGEYE+AEGI +TVFR +LDYYKTGII CPDGISIP+LR+ CDY
SRp20:                36 RMFGPGREYNFTRPNEKGEYEIAEGISATVFRTVLDYYKTGIINCPDGISIPDLRDTCDY  95

Human SR Splicing    255 LCISFEYSTIKCRDLSALMHELSNDGARRQFEFYLEFMILPLMVASAQSGERECHIVVLT 314
Factor 52:               LCI+F+++TI+C+DLSAL+HELSNDGA +QF+ YLEE+ILP+MV  A+ GERECHIVVLT
SRp20:                96 LCINFDFNTIRCQDLSALLHELSNDGAHKQFDHYLEELILPIMVGCAKKGERECHIVVLT 155

Human SR Splicing    315 DDDVVDWDEEYPPQMGEEYSQIIYSTKLYRFFKYIENRDVAKSVLKERGLKKIRLGIEGY 374
Factor 52:               D+D VDWDE++PP MGEEYSQI+YS+KLYRFFKYIENRDVAK+VLKERGLK IR+GIEGY
SRp20:               156 DEDSVDWDEDHPPPMGEEYSQILYSSKLYRFFKYIENRDVAKTVLKERGLKNIRIGIEGY 215

Human SR Splicing    375 PTYKEKVKKRPGGRPEVIYNYVQRPFIRMSWEKEEGKSRHVDFQCVKSKSITNLAAAAAD 434
Factor 52:               PT KEK+K+RPGGR EVIYNYVQRPFI-MSWEKEEGKSRHVDFQCV+SKS+TNL AA  D
SRp20:               216 PTCKEKIKRRPGGRSEVIYNYVQRPFIQMSWEKEEGKSRHVDFQCVRSKSLTNLVAAGDD 275

Human SR Splicing    435 IPQDQLVVMHPTPQVDELDIL--PIHPPSGNSDLD     467
Factor 52:               + +DQ ++MH PQVDELD L  P+    + N  D
SRp20:               276 VLEDQEILMHHPPQVDELDRLNAPLSQMASNDFQD     310
```

Fig. 1

SEQUENCE LISTING

<160> NUMBER OF SEQ ID NOS: 7

<210> SEQ ID NO 1
<211> LENGTH: 2381
<212> TYPE: DNA
<213> ORGANISM: Homo sapiens

<400> SEQUENCE: 1

```
ggaggaagtg gaggtgtcac tggccccggc ctttgcccca atcttgtgtg ggcactgaag      60
ggggactaca ggttcgagag ttatgggtgc tacatgtgtg ctttcagagc agtagtgtga     120
ggaagcttgg agtgggatgg caggacggcc tcatccctat gatggtaact ccagtgatcc     180
agagaattgg gatcggaaat tgcatagtag acctcgtaaa ctttataaac attcaagtac     240
ttcctcgcgt attgctaaag gaggagttga ccacaccaaa atgagtctac atggtgctag     300
tgggggacat gagagatcaa gagatagacg aaggtcaagt gacagatcac gagattcatc     360
tcatgaaaga acggagtccc agctcactcc ttgtattaga aatgtgactt ctccaacacg     420
acagcaccat gttgaacgag aaaaagatca cagttcctct cgtccaagca gtccgcgtcc     480
tcaaaaagca tccccaaatg gttccattag cagtgctggg aacagcagca gaaacagtag     540
tcagtcaagt tcagatggta gctgtaagac agctggggag atggtgtttg tatatgaaaa     600
tgcaaaagaa ggagctcgga atataagaac gtcagaacga gtgacactaa tagtggataa     660
cactagattt gttgtagacc catccatttt tactgcacag ccaaatacaa tgttgggcag     720
gatgtttgga tctggccgag aacataactt tacacgaccc aatgagaaag gagagtatga     780
ggtggcagag ggaattggtt ccactgtgtt tcgagcgatt ctggattact ataaaacagg     840
aataatccgt tgtcctgatg gcatatctat tcctgaactg agagaagcat gtgactatct     900
ttgtatctct tttgaatata gcactattaa atgtagagat ctcagtgccc taatgcatga     960
gttatcaaat gatggtgctc gtagacaatt tgaattttat ctggaagaaa tgatcctccc    1020
tctcatggta gctagtgccc agagtgggga acgggaatgt catatagtgg tgcttacaga    1080
tgatgatgtg gttgattggg atgaagaata tccaccacag atgggagaag aatattcaca    1140
aattatttat agcacaaaat tatatagatt tttcaagtat attgaaaaca gagatgtggc    1200
caagtcagtt ttgaaggaga ggggtcttaa gaagattaga ttgggaatag aaggttatcc    1260
tacctacaaa gaaaaagtaa agaaaaggcc tggaggccgc ccagaagtga tctacaacta    1320
tgtccaaaga ccctttattc gaatgtcctg ggagaaggaa gaaggaaaga gtcggcatgt    1380
agactttcag tgtgtaaaga gtaaatctat caccaatctt gcagcagctg cagcagacat    1440
tccccaggac cagctggtag tcatgcatcc aactccacaa gtggatgagc tggatattct    1500
ccctatccac cccccttctg gcaacagtga cctcgatcct gatgcacaga atccaatgct    1560
gtgatgctga tcttccttga aaccatagca tgctactctt cacagtgacg ttgtactctc    1620
ctcattctgc actgcaaggc cactcttctt cattgtgaga tgcacataac aatgtttagg    1680
atattgcagt gtaggctttt ttaaagacca aggtagctg aatggttttt ttttaaatga    1740
gtacaactct agcattttga agttccagtt gtaaatgtat ttgtttacca gtaggtttgt    1800
gaaattggtt ctttgtatgg gggatggtcc tttttcacac agctaggtct tttcagaagt    1860
ggtggaaatt ggcagctggg gtactttcag tttggactga tattcatcac acctcagata    1920
aaatgcagag taatatatag ttgcacttta taaatggtgg ttaaatggaa atgttcaagc    1980
catttttatag ttgtgatgca caatataatt taagtgcttc tgtcaaagta ttcctccagt    2040
```

-continued

```
acaatttgta tagtttgctg cccttgatga gcaaaaagta tttatcttgg gcttatctga    2100
atgatcagga tgagatttaa tgcccatatc ttaccagttc agttatctcc agagccattt    2160
caccctttag agtgagtcac atgcagggag tgtgaatgtc agaggtggtt tattatccag    2220
tctgccttac ccttaatctg ttcacagata tttatttact aatgcttttt ttttcttaag    2280
agttatggga taggaaaatg aagtgtttgc tcttcattta ctaaatgatt gtaaacttga    2340
gtttttcatc aaaataaaat tccattgttt taatgtttct g                        2381
```

<210> SEQ ID NO 2
<211> LENGTH: 475
<212> TYPE: PRT
<213> ORGANISM: Homo Sapiens

<400> SEQUENCE: 2

```
Met Ala Gly Arg Pro His Pro Tyr Asp Gly Asn Ser Ser Asp Pro Glu
 1               5                  10                  15

Asn Trp Asp Arg Lys Leu His Ser Arg Pro Arg Lys Leu Tyr Lys His
            20                  25                  30

Ser Ser Thr Ser Ser Arg Ile Ala Lys Gly Gly Val Asp His Thr Lys
        35                  40                  45

Met Ser Leu His Gly Ala Ser Gly Gly His Glu Arg Ser Arg Asp Arg
    50                  55                  60

Arg Arg Ser Ser Asp Arg Ser Arg Asp Ser Ser His Glu Arg Thr Glu
65                  70                  75                  80

Ser Gln Leu Thr Pro Cys Ile Arg Asn Val Thr Ser Pro Thr Arg Gln
                85                  90                  95

His His Val Glu Arg Glu Lys Asp His Ser Ser Ser Arg Pro Ser Ser
            100                 105                 110

Pro Arg Pro Gln Lys Ala Ser Pro Asn Gly Ser Ile Ser Ser Ala Gly
        115                 120                 125

Asn Ser Ser Arg Asn Ser Ser Gln Ser Ser Ser Asp Gly Ser Cys Lys
    130                 135                 140

Thr Ala Gly Glu Met Val Phe Val Tyr Glu Asn Ala Lys Glu Gly Ala
145                 150                 155                 160

Arg Asn Ile Arg Thr Ser Glu Arg Val Thr Leu Ile Val Asp Asn Thr
                165                 170                 175

Arg Phe Val Val Asp Pro Ser Ile Phe Thr Ala Gln Pro Asn Thr Met
            180                 185                 190

Leu Gly Arg Met Phe Gly Ser Gly Arg Glu His Asn Phe Thr Arg Pro
        195                 200                 205

Asn Glu Lys Gly Glu Tyr Glu Val Ala Glu Gly Ile Gly Ser Thr Val
    210                 215                 220

Phe Arg Ala Ile Leu Asp Tyr Tyr Lys Thr Gly Ile Ile Arg Cys Pro
225                 230                 235                 240

Asp Gly Ile Ser Ile Pro Glu Leu Arg Glu Ala Cys Asp Tyr Leu Cys
                245                 250                 255

Ile Ser Phe Glu Tyr Ser Thr Ile Lys Cys Arg Asp Leu Ser Ala Leu
            260                 265                 270

Met His Glu Leu Ser Asn Asp Gly Ala Arg Arg Gln Phe Glu Phe Tyr
        275                 280                 285

Leu Glu Glu Met Ile Leu Pro Leu Met Val Ala Ser Ala Gln Ser Gly
    290                 295                 300

Glu Arg Glu Cys His Ile Val Val Leu Thr Asp Asp Asp Val Val Asp
```

```
                305                 310                 315                 320
Trp Asp Glu Glu Tyr Pro Pro Gln Met Gly Glu Tyr Ser Gln Ile
                325                 330                 335
Ile Tyr Ser Thr Lys Leu Tyr Arg Phe Phe Lys Tyr Ile Glu Asn Arg
                340                 345                 350
Asp Val Ala Lys Ser Val Leu Lys Glu Arg Gly Leu Lys Lys Ile Arg
                355                 360                 365
Leu Gly Ile Glu Gly Tyr Pro Thr Tyr Lys Glu Lys Val Lys Lys Arg
        370                 375                 380
Pro Gly Gly Arg Pro Glu Val Ile Tyr Asn Tyr Val Gln Arg Pro Phe
385                 390                 395                 400
Ile Arg Met Ser Trp Glu Lys Glu Glu Gly Lys Ser Arg His Val Asp
                405                 410                 415
Phe Gln Cys Val Lys Ser Lys Ser Ile Thr Asn Leu Ala Ala Ala Ala
                420                 425                 430
Ala Asp Ile Pro Gln Asp Gln Leu Val Val Met His Pro Thr Pro Gln
                435                 440                 445
Val Asp Glu Leu Asp Ile Leu Pro Ile His Pro Pro Ser Gly Asn Ser
        450                 455                 460
Asp Leu Asp Pro Asp Ala Gln Asn Pro Met Leu
465                 470                 475

<210> SEQ ID NO 3
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 3
ggaggaagtg gaggtgtcac tgg                                          23

<210> SEQ ID NO 4
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 4
cagaaacatt aaaacaatgg aa                                           22

<210> SEQ ID NO 5
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 5
ccccatatga tggcaggacg gcctcatccc tatg                              34

<210> SEQ ID NO 6
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 6
catggatcct cacagcattg gattctgtgc atca                              34
```

```
<210> SEQ ID NO 7
<211> LENGTH: 15
<212> TYPE: PRT
<213> ORGANISM: Homo Sapiens

<400> SEQUENCE: 7

Met Ala Gly Arg Pro His Pro Tyr Asp Gly Asn Ser Ser Asp Pro
1               5                   10                  15
```

POLYPEPTIDE— HUMAN SR SPLICING FACTOR 52 AND A POLYNUCLEOTIDE ENCODING THE SAME

FIELD OF THE INVENTION

The invention relates to the field of biotechnology. In particular, the invention relates to a novel polypeptide, human SR splicing factor 52, and a polynucleotide sequence encoding said polypeptide. The invention also relates to the method for the preparation and use of said polynucleotide and polypeptide.

TECHNICAL BACKGROUND

SR proteins are a family of evolutionaly conserved proteins that are related to the regulation of Pre-mRNA natural and alternative splicing. The N-terminal of mammalian SR proteins consist of one or two specific RNA binding domain (RBD). The first RBD(RBD1) has two characteristic and conserved motifs: RNP-1 and RNP-2. RNP-1 and RNP-2 are involved in interacting with DNA. All members of RBD1 have the characteristic sequence ROAEDA. SR family members that have two RBDs have the characteristic sequence SWQDLKD in the second RBD(RBD2). There are no RNP-1 and RNP-2 motifs in the second RBD(RBD2). The C-terminal of SR proteins contains a domain rich in arginine and serine (RS domain). The SR protein family was named after this domain (A. M. Zahler, et al., 1993; T. Gross, et al., 1999).

SR proteins can bind to so-called enhancer sequence and activate the splicing of the weak upstream intron (Reed, et al., 1996; Staknis et al., 1994). RS domain can be phosphorylated by two protein kinase, Clk/Sty and SRPK1. For RS domain to be activated, the phosphorylation is required (Xiao S. H. and Manley 1997).

In mammals, overexpression of SR splicing factor ASF/SF2 will depress the splicing of pre-mRNA, and so does overexpression of the RS domain in variant (Mount S. M. 1997; Gross T et al., 1999).

Factor Srp20 belongs to a highly conserved SR family. It plays multiple roles in the regulation of natural splicing and alternative splicing. During the assembly of the spliceosome, SR is involved in the positioning of the splicing sites. SR proteins can restore splicing ability to cell extracts that lack splicing activity, (e.g. the S-100 cell extracts). Some SR factors have different effect on some alterative splicing sites (Jumaa H et al., 1997; Jumaa H et al., 1999).

Moreover, inactivation of two SR factor, B52/SRp55 in *Drosophila* and ASF/SF2 in chicken cell line DT40, are lethal and lead to the death of young embryos. In transgenic mouse comprising Cre-loxp expression of the SRp20 gene was repressed, and implanted preembryo in transgenic mouse can not form into blastophere and will die in morula stage, indicating that Srp20 plays in important role in development. Immunofluorescence shows that Srp20 is expressed in oocyte and early stages of embryo genesis (Ring H Z, et al., 1994; Petersen-Mahrt S K, et al., 1999; Jumaa H, et al., 1999).

The human polypeptide gene in the present invention shares 75% protein-level homology with human SRp20 (database accession #Z85986). The inventive protein has an apparent molecular weight ot 52.2 KD and comprises 475aa). It also contains characteristic domains of the SR family, that is, the N-terminal has one or two specific RNA binding domains (RBD). The first RBD(RBD1) have conserved RNP-1 and RNP-2 motifs, involved in interacting with DNA. All members of RBD1 have characteristic sequence RDAEDA. The SR family members that have two RBDs have the characteristic sequence SWQDLKD in the second RBD(RBD2). There is no RNP-1 and RNP-2 motif in the second RBD(RBD2). The C-terminal of RBD2 has an RS domain rich in arginine and serine (RS domain). The new gene of the present invention is found to be one member of SR family and was named SR splicing factor 52. It was found that the human SR splicing factor 52 has similar biology function as that of the SR splicing factor family.

The discovery of human SR splicing factor 52 polypeptide and its gene provides a method for studying the physiology and biochemistry of cell differentiation and proliferation under normal and pathological conditions. It also provides a new diagnosis and treatment method for diseases caused by abnormality of the cell differentiation and proliferation, including cancer.

As discussed, human SR splicing factor 52 plays an essential role in the regulation of important biological functions such as cell division and embryogenesis, and it's believed that numerous proteins are involved in these regulations. So the identification of the human SR splicing factor 52, especially its amino acid sequence, is always desired in this filed. The isolation of this novel human SR splicing factor 52 builds the basis for research of the protein function under normal and clinical conditions, disease diagnosis and drug development. So the isolation of its cDNA is very important.

DESCRIPTION OF THE INVENTION

One objective of the invention is to provide an isolated novel polypeptide, i.e., a human SR splicing factor 52, and fragments, analogues and derivatives thereof.

Another objective of the invention is to provide a polynucleotide encoding said polypeptide.

Another objective of the invention is to provide a recombinant vector containing a polynucleotide encoding a human SR splicing factor 52.

Another objective of the invention is to provide a genetically engineered host cell containing a polynucleotide encoding a human SR splicing factor 52.

Another objective of the invention is to provide a method for producing a human SR splicing factor 52.

Another objective of the invention is to provide an antibody against a human SR splicing factor 52 of the invention.

Another objective of the invention is to provide mimetics, antagonists, agonists, and inhibitors for the polypeptide of the human SR splicing factor 52.

Another objective of the invention is to provide a method for the diagnosis and treatment of the diseases associated with an abnormality of human SR splicing factor 52.

The present invention relates to an isolated polypeptide, which is originated from human, and comprises a polypeptide having the amino acid sequence of SEQ ID NO: 2, or its conservative variants, or its active fragments, or its active derivatives and its analogues. Preferably, the polypeptide has the amino acid sequence of SEQ ID NO: 2.

The present invention also relates to an isolated polynucleotide, comprising a nucleotide sequence or its variant selected from the group consisting of (a) the polynucleotide encodeing a polypeptide comprising the amino acid sequence of SEQ ID NO: 2; and (b) a polynucleotide complementary to the polynucleotide (a);(c) a polynucleotide that shares at least 70% homology to the polynucleotide (a) or (b). Preferably, said nucleotide sequence is selected from the group consisting of (a) the sequence of position 225–664 in SEQ ID NO: 1; and (b) the sequence of position 1–775 in SEQ ID NO: 1.

The invention also includes: a vector containing a polynucleotide of said invention, especially an expression vector; a host cell genetically engineered with the vector via transformation, transduction or transfection; a method for the production of said inventive polypeptide through the process of host cell cultivation and expession product harvest.

The invention also relates to an antibody which specifically binds to the inventive polypeptide.

The invention also relates to a method for selecting compounds which could simulate, activate, antagonize, or inhibit the activity of the inventive polypeptide and the compounds obtained by the method.

The invention also relates to a method for in vitro diagnosis method of the diseases or disease susceptibility related with the abnormal expression of the inventive polypeptide. The method involves the detection of mutation in the polypeptide or its encoding polynucleotide sequence, or the determination of its quantity and/or biological activity in biological samples.

The invention also relates to pharmaceutical compositions which comprises the inventive polypeptide, its analogues, mimetics, agonists, antagonists, inhibitors, and a pharmaceutically acceptable carrier.

The invention also relates to applications of the inventive polypeptide and/or its polynucleotide for drug development to treat cancers, developmental diseases, immune diseases, or other diseases caused by abnormal expression of the inventive polypeptide.

Other aspects of the invention are apparent to the skilled in the art in view of the disclosure set forth hereinbelow.

The terms used in this specification and claims have the following meanings, unless otherwise noted.

"Nucleotide sequence" refers to oligonucleotide, nucleotide, or polynucleotide and parts of polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in the invention is related to the sequence of a natural protein, the amino acid sequence of said "peptide" or "protein" will not be limited to be identical to the sequence of that natural protein.

"Variant" of a protein or polynucleotide refers to the amino acid sequence or nucleotide sequence, respectively with one or more amino acids or one or more nucleotides changed. Such changes include deletion, insertion, and/or substitution of amino acids in the animo acid sequence, or of nucleotides in the polynucleotide sequence. These changes could be conservative and the substituted amino acid has similar structural or chemical characteristics as the original one, such as the substitution of Ile with Leu. Changes also could be not conservative, such as the substitution of Ala with Trp.

"Deletion" refers to the deletion of one or several amino acids in the amino acid sequence, or of one or several nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing number of the residues.

"biological activity" refers to structural, regulatory or biochemical characteristics of a natural molecule. Similarly, the term "immungenecity" refers to the ability of natural, recombinant, or synthetic proteins to inducing a specific immunologic reaction, or of binding specific antibody in appropriate kind of animal or cell.

"Agonist" refers to molecules which regulate, but generally enhance the activity of the inventive polypeptide by binding and changing it. Agonists include proteins, nucleotides, carbohydrates or any other molecules which could bind the inventive polypeptide.

"Antagonist" or "inhibitor" refers to molecules which inhibit or downregulate the biological activity or immunogenecity the inventive polypeptide via binding to it. Antagonists or inhibitors include proteins, nucleotides, carbohydrates or any other molecules which bind to the inventive polypeptide.

"regulation" refers to changes in function of the inventive polypeptide, including up-regulation or down-regulation of the protein activity, changes in binding specifity, changes of any other biological characteristics, functional or immune characteristics.

"Substantially pure" refers to the condition of substantially free of other naturally related proteins, lipids, saccharides, or other substances. One of ordinary skill in the art can purify the inventive polypeptide by standard protein purification techniques. Substantially pure polypeptide of the invention produces a single main band in a denaturing polyacrylamide gel. The purity of a polypeptide may also be analyzed by amino acid sequence analysis.

"Complementary" or "complementation" refers to the binding of polynucleotides by base pairing under the condition of approximate ion conditions and temperature. For instance, the sequence "C-T-G-A" could bind its complementary sequence "G-A-C-T." The complementation between two single strand molecules could be partial or complete. Homology or sequence similarity between two single strands obviously influences the efficiency and strength of the formed hybrid.

"Homology" refers to the complementary degree, which may be partially or completely homologous. "Partial homology" refers to a sequence being partially complementary to a target nucleotide. The sequence could at least partially inhibit the hybridization between a completely complementary sequence and the target nucleotide. Inhibition of hybridization could be assayed by hybridization (Southern blot or Northern blot) under less stringent conditions. Substantially complementary sequence or hybrid probe could compete with the completely complementary sequence and inhibit its hybridization with the target sequence under less stringent conditions. This doesn't mean that nonspecific binding is allowed under a less stringent condition, because specific or selective reaction is still required.

"Sequence Identity" refers to the percentage of sequence identity or similarity when two or several amino acid or nucleotide sequences are compared. Sequence identity may be determined by computer programs such as MEGALIGN (Lasergene Software Package, DNASTAR, Inc., Madison Wis.). MEGALIGN can compare two or several sequences using different methodologies such as the Cluster method (Higgins, D. G. and P. M. Sharp (1988) Gene 73: 237–244). Cluster method examines the distance between all pairs and arrange the sequences into clusters. Then the clusters are partitioned by pair or group. The sequence identity between two amino acid sequences such as sequence A and B can be calculated by the following equation:

$$\frac{\text{Number of paired identical residues between sequences } A \text{ and } B}{\text{Residue number of sequence } A - \text{number of gap residues in sequence } A - \text{number of gap residue in sequence } B} \times 100$$

Sequence identity between nucleotide sequences can also be determined by Cluster method or other well-known methods in the art such as the Jotun Hein method (Hein J., (1990) Methods in Emzymology 183: 625–645).

"Similarity" refers to the degree of identity or conservative substitution degree of amino acid residues in corresponding sites of the amino acid sequences when compared to each other. Amino acids for conservative substitution are: negative charged amino acids including Asp and Glu; positive charged amino acids including Leu, Ile and Val; Gly and Ala; Asn and Gln; Ser and Thr; Phe and Tyr.

"Antisense" refers to the nucleotide sequences complementary to a specific DNA or RNA sequence. "Antisese strand" refers to the nucleotide strand complementary to the "sense strand."

"Derivative" refers to the inventive polypeptide or the chemically modified nucleotide encoding it. This kind of modified chemical can be derived from replacement of the hydrogen atom with Alkyl, Acyl, or Amino. The nucleotide derivative can encode peptide retaining the major biological characteristics of the natural molecule.

"Antibody" refers to the intact antibody or its fragments such as Fa, F(ab')2 and Fv, and it can specifically bind to antigenic epitopes of the inventive polypeptide.

"Humanized antibody" refers to an antibody which has its amino acid sequence in non-antigen binding region replaced to mimic human antibody and still retain the original binding activity.

The term "isolated" refers to the removal of a material out of its original environment (for instance, if it's naturally produced, original environment refers to its natural environment). For example, a naturally produced polynucleotide or a polypeptide in its original host organism means it has not been "isolated," while the separation of the polynucleotide or a polypeptide from its coexisting materials in natural system means it was "isolated." This polynucleotide may be a part of a vector, or a part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human SR splicing factor 52," means that human SR splicing factor 52 does not essentially contain other proteins, lipids, carbohydrate or any other substances associated therewith in nature. The skilled in the art can purify human SR splicing factor 52, by standard protein purification techniques. The purified polypeptide forms a single main band on a non-reducing PAGE gel. The purity of human SR splicing factor 52 can also be analyzed by amino acid sequence analysis.

The invention provides a novel polypeptide—human SR splicing factor 52, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human SR splicing factor 52. As used in the invention, the terms "fragment," "derivative" and "analogue" mean the polypeptide that essentially retains the same biological functions or activity of human SR splicing factor 52 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 2381 bp, whose ORF (137–1564) encodes 475 amino acids. Based on amino acid homology comparison, it is found that the encoded polypeptide is 75% homologous to SRp20. This novel human protein phosphatase regulatory protein 68 has similar structures and biological functions to those of SRp20.

The polynucleotide according to the invention may be in the forms of DNA or RNA. The forms of DNA include cDNA, genomic DNA, and synthetic DNA, etc., in single stranded or double stranded form. DNA may be an encoding strand or a non-encoding strand. The coding sequence for mature polypeptide may be identical to the coding sequence shown in SEQ ID NO: 1, or is a degenerate sequence. As used herein, the term "degenerate sequence" means a sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polyaucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2.

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding human SR splicing factor 52.

The polypeptide and polynucleotide of the invention are preferably in the isolated form, preferably purified to be homogenous.

According to the invention, the specific nucleic acid sequence encoding human SR splicing factor 52 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human SR splicing factor 52 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleocides, preferably at least 30 nucleocides, more preferably at least 50 nucleocides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human SR splicing factor 52 gene can be carried out by immunology methods, such as Western blotting, radioimmunoassay, and ELISA.

The method of amplification of DNA/RNA by PCR (Saiki, et al. Science 1985; 230: 1350–1354) is preferably used to obtain the polynucleotide of the invention. Especially when it is difficult to obtain the full-length cDNA, the method of RACE (RACE-cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing lits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human SR splicing factor 52, and a method for producing the polypeptide of the invention by recombinant techniques.

In the present invention, the polynucleotide sequences encoding human SR splicing factor 52 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56: 125, 1987), the pMSXND expression vector for expression in mammalian cells (Lee and Nathans, J Biol. Chem., 263: 3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human SR splicing factor 52 and appropriate transcription/ translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of $E.$ $coli$; PL promoter of $\lambda$ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.$ $coli.$ An ordinarily skilled in the art know clearly how to select appropriate vectors, transcriptional regulatory elements, e.g., promoters, enhancers, and selective marker genes.

According to the invention, polynucleotide encoding human SR splicing factor 52 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as $E.$ $coli,$ $Streptomyces,$ $Salmonella$ $typhimurium$; fungal cells, such as yeast; plant cells; insect cells such as $Drosophila$ S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as $E.$ $coli$, competent cells, which are capable of DNA uptake, can be prepared from cells harvested after exponential growth phase and subsequently treated by the CaCl2 method using procedures well known in the art. Alternatively, MgCl2 can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human SR splicing factor 52 can be expressed or produced by the conventional recombinant DNA technology (Science, 1984; 224: 1431), using the polynucleotide sequence of the invention. The steps generally include:

(1) transfecting or transforming the appropriate host cells with the polynucleotide (or variant) encoding human SR splicing factor 52 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

BRIEF DESCRIPTION OR THE DRAWINGS

FIG. 1 shows an alignment comparison of amino acid sequences of human SR splicing factor 52 of the invention and SRp20. The upper sequence is human SR splicing factor 52, and the lower sequence is SRp20. The identical and similar amino acids are indicated by a one-letter code of amino acid and "+" respectively.

FIG. 2 shows the SDS-PAGE of the isolated human SR splicing factor 52, which has a molecular weight of 52 kDa. The isolated protein band is marked with an arrow.

EXAMPLES

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Cloning of Human SR Splicing Factor 52 Gene

Total RNA from a human embryonic brain was extracted by the one-step method with guanidinium isocyanate/phenollchloroform. The poly(A) mRNA was isolated from the total RNA with Quik mRNA Isolation Kit (Qiegene). cDNA was prepared by reverse transcription with 2 μg poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 0930E07 was found to be a novel DNA sequence. The inserted cDNA sequence of clone 0930E07 was dual-directionally sequenced with a serial of synthesized primers. It was indicated that the full length cDNA contained in clone 0930E07 was 2381 bp (SEQ ID NO: 1) with a 1428 bp ORF located in positions 137–1564 which encoded a novel protein (SEQ ID NO: 2). This clone was named pBS-0930E07 and the encoded protein was named human SR splicing factor 52.

Example 2

Homology Search of cDNA Clone

The homology research of the DNA sequence and its protein sequence of human SR splicing factor 52 of the invention were performed by Blast (Basic Local Alignment Search Tool) (Altschul, S F et al. J. Mol. Biol. 1990; 215: 403–10) in databases such as Genbank, Swissport, etc. The most homologous gene to human SR splicing factor 52 of the invention is known (SRp20). The Genbank accession number of its encoded protein is Z85986. The alignment result of the protein was shown in FIG. 1. Two proteins are highly homologous with an identity of 75% and a similarity of 88%.

Example 3

Cloning Human SR Splicing Factor 52 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

Primer 1: 5'-GGAGGAAGTGGAGGTGTCACTGG-3' (SEQ ID NO: 3)

Primer 2: 5'-CAGAAACATTAAAACAATGGAA-3' (SEQ ID NO: 4)

Primer 1 is the forward sequence started from position 1 of 5' end of SEQ ID NO: 1.

Primer 2 is the reverse sequence of the 3' end of SEQ ID NO: 1.

The amplification condition was a 50 ul reaction system containing 50 mmol/L KCl, 10 mmol/L Tris-Cl (pH8.5), 1.5 mmol/L $MgCl_2$, 200 umol/L dNTP, 10 pmol of each primer, 1U Taq DNA polymerase(Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–2381 bp of SEQ ID NO: 1.

Example 4

Northern Blotting of Expression of Human SR Splicing Factor 52 Gene

Total RNA was extracted by one-step method (Anal. Biochem 1987, 162, 156–159) with guanidinium isocyanate-phenol-chloroform. That is, homogenate the organize using 4M guanidinium isocyanate-25 mM sodium citrate, 0.2M sodium acetate (pH4.0), add 1 volume phenol and 1/5 volume chloroform-isoamyl alcohol(49:1), centrifuge after mixing. Take out the water phase, add 0.8 volume isopropyl alcohol, then centrifuge the mixture. Wash the RNA precipitation using 70% ethanol, then dry, then dissolve it in the water. 20 μg RNA was electrophoresed on the 1.2% agarose gel containing 20 mM 3-(N-morpholino) propane sulfonic acid(pH7.0)-5 mM sodium acetate-1 mM EDTA-2.2M formaldehyde. Then transfer it to a nitrocellulose filter. Prepare the $^{32}P$-labelled DNA probe with $\alpha$-$^{32}P$ dATP by random primer method. The used DNA probe is the coding sequence (137 bp–1564 bp) of human SR splicing factor 52 amplified by PCR indicated in FIG. 1. The nitrocellulose filter with the transferred RNA was hybridized with the $^{32}P$-labelled DNA probe ($2\times10^6$ cpm/ml) overnight in a buffer containing 50% formamide-25 mM $KH_2PO_4$ (Ph7.4)-5×Denhardt's solution and 200 μg/ml salmine. Then wash the filter in the 1×SSC-0.1% SDS, at 55° C., for 30 min. Then analyze and quantitative determinate using Phosphor Imager.

Example 5

In vitro Expression, Isolation and Purification of Recombinant Human SR Splicing Factor 52

A pair of primers for specific amplification was designed based on SEQ ID NO: 1 and the encoding region in FIG. 1, the sequences are as follows:

Primer 3: 5'-CCCCATATGATGGCAGGACGGCCTCATCCCTATG-3' (SEQ ID NO: 5)

Primer 4: 5'-CATGGATCCTCACAGCATTGGATTCTGTGCATCA-3' (SEQ ID NO: 6).

These two primers contain a NdeI and BamHI cleavage site on the 5' end respectively. Within the sites are the coding sequences of the 5' and 3' end of the desired gene. NdeI and BamHI cleavage sites were corresponding to the selective cleavage sites on the expression vector pET-28b(+) (Novagen, Cat. No. 69865.3). PCR amplification was performed with the plasmid pBS-0930E07 containing the full-length target gene as a template. The PCR reaction was subject to a 50 μl system containing 10 pg pBS-0930E07 plasmid, 10 pmol of Primer-3 and 10 pmol of Primer-4, 1 μl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NdeI and BamHI, the large fragments were recovered and ligated with T4 ligase. The ligated product was transformed into *E. coli* DH5α with the calcium chloride method. After cultured overnight on a LB plate containing a final concentration of 30 μg/ml kanamycin, positive clones were selected out using colony PCR and then sequenced. The positive clone (pET-0930E07) with the correct sequence was selected out and the recombinant plasmid thereof was transformed into BL21(DE3) plySs (Novagen) using the calcium chloride method. In a LB liquid medium containing a final concentration of 30 μg/ml of kanamycin, the host bacteria BL21(pET-0930E07) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—human SR splicing factor 52 was obtained by a His.Bind Quick Cartridge (Novagen) affinity column with binding 6His-Tag. SDS-PAGE showed a single band at 52 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

Example 6

Preparation of Antibody Against Human SR Splicing Factor 52

The following specific human SR splicing factor 52 polypeptide was synthesized by a polypeptide synthesizer (PE-ABI): NH2-Met-Ala-Gly-Arg-Pro-His-Pro-Tyr-Asp-Gly-Asn-Ser-Ser-Asp-Pro-COOH (SEQ ID NO: 7). The polypeptide was conjugated with hemocyanin and bovine serum albumin (BSA) respectively to form two composites (See Avrameas et al., Immunochemistry, 1969, 6: 43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 μg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinty chromatography. The immunoprecipitation approved that the purified antibodies could specifically bind to human SR splicing factor 52.

INDUSTRIAL APPLICABILITY

The polypeptide of the invention and its antagonist, agonist and inhibitor can be used for treating diseases such as various malignant tumors, adrenoprival disease, dermatitis, inflammation, HIV infection and immune system diseases directly.

SR protein family is related to the regulation of pre-mRNA native and alternative splicing. In mammals, overexpression of SR splicing factor ASF/SF2 will depress the splicing of pre-mRNA, and so does the overexpression of the RS domain variant. (Mount S M 1997; Gross T et al., 1999).

Inactivation of two SR factor, B52/SRp55 of *Drosophila* and ASF/SF2 of chicken cell line DT40, was found to lead to the death of young embryo. Studies with transgenic mice that have inhibited SRp20 gene expression show that Srp20 is important for development. Preembryo implanted into mutant mice can not form blastophere and will die in the morula stage. Immunofluorescence studies show that Srp20 is expressed in oocyte and during early developing stages of embryo (Ring H Z, et al., 1994; Petersen-Mahrt S K, et al., 1999; Jumaa H, et al., 1999).

It is thus clear that abnormal expression of human SR splicing factor 52 of the invention will lead to many diseases, especially congenital abortion, and congenital deformity. Other disease include, but are not limited to:

Deformity of the face, neck, limbs, such as cleft lip, cleft palate, oblique facial cleft, cervical cyst, and cervical fistula;

Common deformities of limbs, such as congenital absence of the limbs, anbrachia, absence of the forearms, absence of the hands, acheiria, absence of the legs, absence of toes; longitudinal limb defects: upper limb radialis or ulnaris defeciency, lower limb tibial or fibular defect, Phocomelia; limb differentiation disorder: including defect of certain muscle or muscle group, dysplasia development of arthron, bone deformity, bone confluence, polydactyly, Syndactyly, equinovarus and so on.

Common deformity of digestive system: thyroglossal cyst, digestion tube atresia or cinstriction, Diverticulum of ileum, umbilical fistula, congenital unbilical hernia, congenital aganglia giant colon, imperforate anus, boweltanslocation abnormality, biliary atresia, Annular pancreas.

Common deformity of respiratory system: tracheal stenosis, tracheal atresia, tracheo-esophageal fistula, hyaline membrane disease, unilateral pulmonary agenesis, ectopic lung lobe, congenital pulmonary cyst, atelectasis.

Common deformity of urinary system: polycystic kidney, ectopic kicney, horse-type kidney, double ureter, urachal fistula, ectopia vesicae.

Common deformity of genital system: cryptorchidism, congenital inguinal hernia, double uterus, vaginal atresia, hypospadia, hermaphrodism, androgen insensitibity syndrome.

Common deformity of cardiovascular system: arterial septal defect, ventricular septal defect, trunus arteriosus partition abnormity such as displacement of hemal axis and pulmonary artery, aortic stenosis, pulmonary artery stenosis, patent arterial duct.

Common deformity of nervous system: neural tube defect, hydrocephalus.

Common deformity of the eye and ear: coloboma iridis, congenital catarct, congenital glaucoma, microphthalmia deformity, congenital deafniess, auricle deformity.

Abnormal expression of human SR splicing factor 52 in the said invention will also lead to some metabolism disorder disease, tumor, ingerited disease, nervous system disease, hematopathy and disease of immune system.

The invention also provides methods for screening compounds so as to identify an agent which enhances human SR splicing factor 52 activity (agonists) or decrease human SR splicing factor 52 activity (antagonists). The agonists enhance the biological functions of human SR splicing factor 52 such as inactivation of cell proliferation, while the antagonists prevent and cure the disorders associated with the excess cell proliferation, such as various cancers. For example, in the presence of an agent, the mammal cells or the membrane preparation expressing human SR splicing factor 52 can be incubated with the labeled human SR splicing factor 52 to determine the ability of the agent to enhance or inhibit the interaction.

Antagonists of human SR splicing factor 52 include antibodies, compounds, receptor deletants and analogues. The antagonists of human SR splicing factor 52 can bind to human SR splicing factor 52 and eliminate or reduce its function, or inhibit the production of human SR splicing factor 52, or bind to the active site of said polypeptide so that the polypeptide can not function biologically.

When screening for compounds as an antagonist, human SR splicing factor 52 may be added into a biological assay. It can be determined whether the compound is an antagonist or not by determining its effect on the interaction between human SR splicing factor 52 and its receptor. Using the same method as that for screening compounds, receptor deletants and analogues acting as antagonists can be selected. Polypeptide molecules capable of binding to human SR splicing factor 52 can be obtained by screening a polypeptide library comprising various combinations of amino acids bound onto a solid matrix. Usually, human SR splicing factor 52 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of human SR splicing factor 52. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with human SR splicing factor 52. Various adjuvants, including but are not limited to Freund's adjuvant, can be used to enhance the immunization. The techniques for producing human SR splicing factor 52 monoclonal antibodies include, but are not limited to, the hybridoma technique (Kohler and Milstein. Nature, 1975, 256: 495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81: 6851). Furthermore, techniques for producing a single-chain antibody (U.S. Pat. No. 4,946,778) are also useful for preparing single-chain antibodies against human SR splicing factor 52.

The antibody against human SR splicing factor 52 can be used in immunohistochemical method to detect the presence of human SR splicing factor 52 in a biopsy specimen.

The monoclonal antibody specific to human SR splicing factor 52 can be labeled by radioactive isotopes, and injected into human body to trace the location and distribution of human SR splicing factor 52. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to human SR splicing factor 52 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill human SR splicing factor 52-positive cells.

The antibody of the invention is useful for the therapy or the prophylaxis of disorders related to the human SR splicing factor 52. The appropriate amount of antibody can be administrated to stimulate or block the production or activity of human SR splicing factor 52.

The invention further provides diagnostic assays for quantitative and in situ measurement of human SR splicing factor 52 level. These assays are well known in the art and include FISH assay and radioimmunoassay. The level of human SR splicing factor 52 detected in the assay can be used to illustrate the importance of human SR splicing factor 52 in diseases and to determine the diseases associated with human SR splicing factor 52.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New human SR splicing factor 52 polynucleotides also have many therapeutic applications. Gene therapy technology can be used in the therapy of abnormal cell proliferation, development or metabolism, which are caused by the loss of human SR splicing factor 52 expression or the abnormal or non-active expression of human SR splicing factor 52. Recombinant gene therapy vectors, such as virus vectors, can be designed to express mutated human SR splicing factor 52 so as to inhibit the activity of endogenous human SR splicing factor 52. For example, one form of mutated human SR splicing factor 52 is a truncated human SR splicing factor 52 whose signal transduction domain is deleted. Therefore, this mutated human SR splicing factor 52 can bind the downstream substrate without the activity of signal transduction. Thus, the recombinant gene therapy vectors can be used to cure diseases caused by abnormal expression or activity of human SR splicing factor 52. The expression vectors derived from a virus, such as retrovirus, adenovirus, adeno-associated virus, herpes simplex virus, parvovirus, and so on, can be used to introduce the human SR splicing factor 52 gene into the cells. The methods for constructing a recombinant virus vector harboring human SR splicing factor 52 gene are described in the literature (Sambrook, et al. supra). In addition, the recombinant human SR splicing factor 52 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the human SR splicing factor 52 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding human SR splicing factor 52 can be used in the diagnosis of human SR splicing factor 52 related diseases. The polynucleotide encoding human SR splicing factor 52 can be used to detect whether human SR splicing factor 52 is expressed or not, and whether the expression of human SR splicing factor 52 is normal or abnormal in the case of diseases. For example, human SR splicing factor 52 DNA sequences can be used in the hybridization with biopsy samples to determine the expression of human SR splicing factor 52. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The human SR splicing factor 52 specific primers can be used in RNA-polymerase chain reaction and in vitro amplification to detect transcripts of human SR splicing factor 52.

Further, detection of mutations in human SR splicing factor 52 gene is useful for the diagnosis of human SR splicing factor 52 -related diseases. Mutations of human SR splicing factor 52 include site mutation, translocation, deletion, rearrangement and any other mutations compared with the wild-type human SR splicing factor 52 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. human SR splicing factor 52 is administered in an amount, which is effective for treating and/or prophylaxis of the specific indication. The amount of human SR splicing factor 52 administrated on patient will depend upon various factors, such as delivery methods, the subject's health, the judgment of the skilled clinician.

We claim:

1. An isolated polynucleotide selected from the group consisting of:
   (a) a polynucleotide encoding a polypeptide that has an SR splicing factor 52 activity and is at least 95% identical to SEQ ID NO: 2; and
   (b) a polynucleotide complementary to polynucleotide (a).

2. A polynucleotide of claim 1 wherein the polynucleotide encodes an amino acid sequence of SEQ ID NO:2.

3. A polynucleotide of claim 1 wherein the sequence of said polynucleotide comprises positions 37–1564 of SEQ ID NO:1.

4. A polynucleotide of claim 3 wherein the sequence of said polynucleotide comprises positions 1–2381 of SEQ ID NO:1.

5. A recombinant vector comprising a polynucleotide of claim 1, and a regulatory element.

6. A genetically engineered host cell comprising a polynucleotide of claim 1.

7. A pharmaceutical composition comprising a polynucleotide according to claim 1, and a pharmaceutically acceptable carrier.

* * * * *